(12) United States Patent
Kaufmann et al.

(10) Patent No.: US 6,673,353 B1
(45) Date of Patent: *Jan. 6, 2004

(54) TUBERCULOSIS VACCINE

(75) Inventors: Stefan H. E. Kaufmann, Berlin (DE); Jürgen Hess, Berlin (DE)

(73) Assignee: Max-Planck-Gesellschaft zur Forderung der Wissenschaften e.V. (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/485,717

(22) PCT Filed: Aug. 12, 1998

(86) PCT No.: PCT/EP98/05109

§ 371 (c)(1),
(2), (4) Date: Feb. 22, 2000

(87) PCT Pub. No.: WO99/10496

PCT Pub. Date: Mar. 4, 1999

(30) Foreign Application Priority Data

Aug. 22, 1997 (EP) .............................. 97114614

(51) Int. Cl.[7] .................. A61K 39/02; A61K 39/04; A61K 45/00; A61K 47/00

(52) U.S. Cl. .............. 424/200.1; 424/9.1; 424/9.2; 424/184.1; 424/185.1; 424/190.1; 424/192.1; 424/203.1; 424/234.1; 424/248.1; 424/278.1; 424/93.1; 424/93.2; 435/320.1; 530/300; 530/350; 536/23.1; 536/23.7

(58) Field of Search .................. 424/9.1, 9.2, 184.1, 424/185.1, 190.1, 192.1, 200.1, 203.1, 248.1, 234.1, 278.1, 93.1, 93.2; 435/320.1; 530/300, 350; 536/23.1, 23.7

(56) References Cited

PUBLICATIONS

Wiegeshaus et al, Evaluation of the protective potency of new tuberculosis vaccines. Reviews of Infectious Diseases vol. 11, Supplement 2, pp. S484–S490, 1989.*

* cited by examiner

*Primary Examiner*—Rodney P Swartz
(74) *Attorney, Agent, or Firm*—Rothwell, Figg, Ernst & Manbeck

(57) ABSTRACT

The present invention relates to novel recombinant vaccines providing protective immunity against tuberculosis. Further, the present invention refers to novel recombinant nucleic acid molecules, vectors containing said nucleic acid molecules, cells transformed with said nucleic acid molecules and polypeptides encoded by said nucleic acid molecules.

33 Claims, 6 Drawing Sheets

Figure 1A:
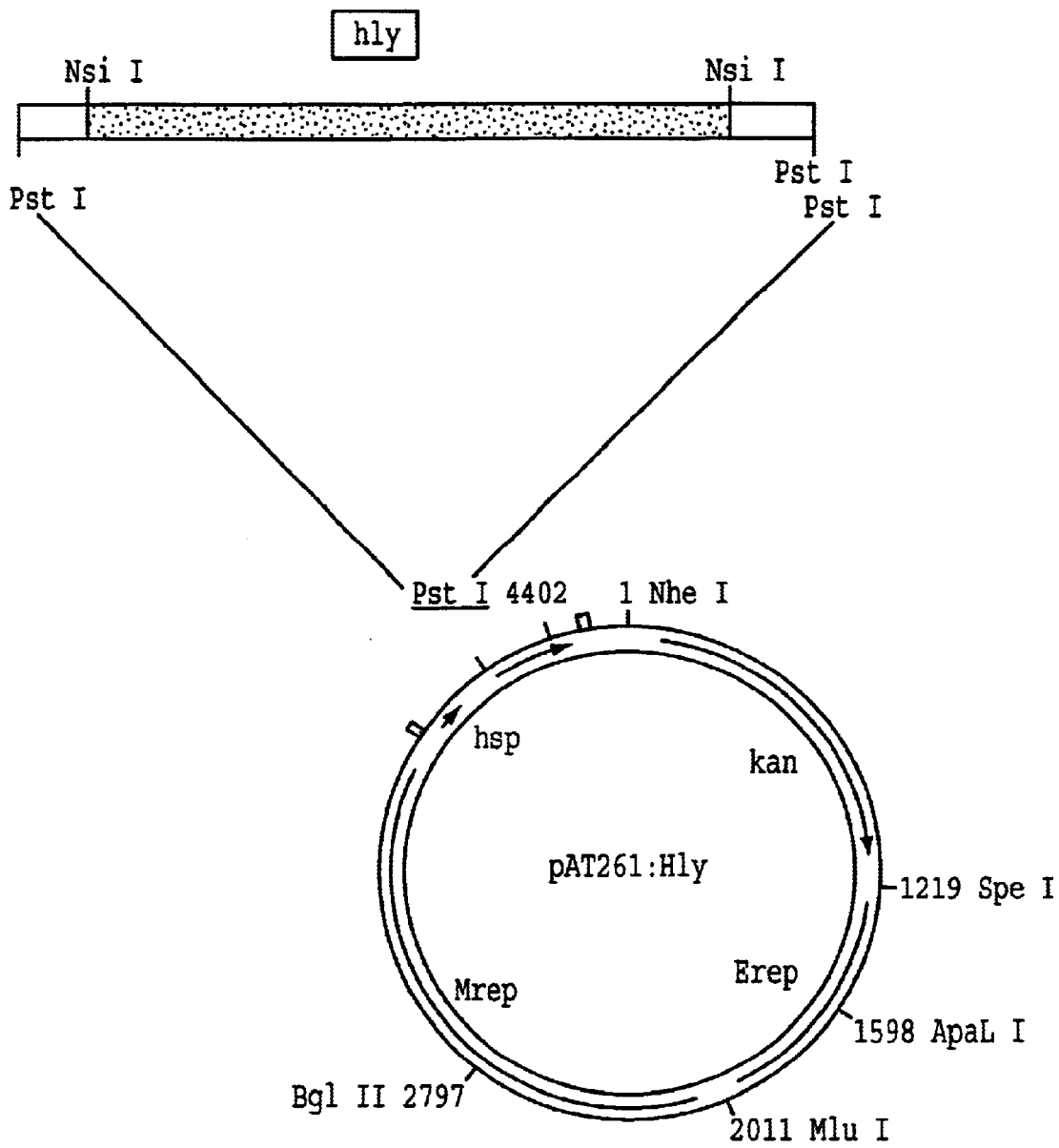

```
     Ag85B signal peptide                 mature Ag85B sequence
                                                    ↓
  1 MTDVSRKIRA WGRRLMIGTA AAVVLPGLVG LAGGAATAGA FSRPGLPVEY Hly A peptide linker   mature Hly sequence
 51 LQSAKQSAAN KLHSAGQSTK DASAFNKENS ISSMAPPASP PASPKTPIEK
   (Pst I)             (Nsi I)

101 KHADEIDKYI QGLDYNKNNV LVYHGDAVTN VPPRKGYKDG NEYIVVEKKK

151 KSINQNNADI QVVNAISSLT YPGALVKANS ELVENQPDVL PVKRDSLTLS

201 IDLPGMTNQD NKIVVKNATK SNVNNAVNTL VERWNEKYAQ AYPNVSAKID

251 YDDEMAYSES QLIAKFGTAF KAVNNSLNVN FGAISEGKMQ EEVISFKQIY

301 YNVNVNEPTR PSRFFGKAVT KEQLQALGVN AENPPAYISS VAYGRQVYLK

351 LSTNSHSTKV KAAFDAAVSG KSVSGDVELT NIIKNSSFKA VTYGGSAKDE

401 VQIIDGNLGD LRDILKKGAT FNRETPGVPI AYTTNFLKDN ELAVIKNNSE

451 YIETTSKAYT DGKINIDHSG GYVAQFNISW DEVNYDPEGN EIVQHKNWSE

501 NNKSKLAHFT SSIYLPGNAR NINVYAKECT GLAWEWWRTV IDDRNLPLVK

HlyA peptide linker
551 NRNISIWGTT LYPKYSNKVD NPIEYALAYG SQGDLNPLIN EISKIISAAV
                             (Nsi I)                   (Pst I)
    random peptide sequence
601 LSSLTSKLPA EFVRRGSGIR SLSMST
         (Pst I)
```

TUBERCULOSIS VACCINE

The present invention relates to novel recombinant vaccines providing protective immunity especially against tuberculosis. Further, the present invention refers to novel recombinant nucleic acid molecules, vectors containing said nucleic acid molecules, cells transformed with said nucleic acid molecules and polypeptides encoded by said nucleic acid molecules.

Tuberculosis (TB) caused by *Mycobacterium tuberculosis* remains a significant global problem. It is estimated that one third of the world's population is infected with *M.tuberculosis* (Kochi, 1991). In many countries the only measure for TB control has been vaccination with *M.bovis* bacille Calmette-Guérin (BCG). The overall vaccine efficacy of BCG against TB, however, is about 50% with extreme variations ranging from 0% to 80% between different field trials (Roche et al., 1995). Thus, BCG should be improved, e.g. by genetic engineering, to provide a vaccine for better TB control (Murray et al., 1996; Hess and Kaufmann, 1993). The widespread emergence of multiple drug-resistant *M.tuberculosis* strains additionally underlines the urgent requirement for novel TB vaccines (Grange, 1996).

*M.tuberculosis* belongs to the group of intracellular bacteria that replicate within the phagosomal vacuoles of resting macrophages, thus protection against TB depends on T cell-mediated immunity (Kaufmann, 1993). Several studies in mice and humans, however, have shown that mycobacteria stimulate antigen-specific, major histocompatibility complex (MHC) class II- or class I-restricted CD4 and CD8 T cells, respectively (Kaufmann, 1993).

The important role of MHC class I-restricted CD8 T cells was convincingly demonstrated by the failure of β2-microglobulin (β2m) deficient mice to control experimental *M.tuberculosis* infection (Flynn et al., 1993). Because these mutant mice lack MHC class I, functional CD8 T cells cannot develop. In contrast to *M.tuberculosis* infection, β2m-deficient mice are capable of controlling certain infectious doses of the BCG vaccine strain (Flynn et al., 1993; Ladel et al., 1995). Furthermore, BCG vaccination of β2m-deficient mice prolonged survival after subsequent *M.tuberculosis* infection whereas BCG-immunized C57BL/6 resisted TB (Flynn et al., 1993). This differential CD8 T cell dependency between *M.tuberculosis* and BCG may be explained as follows: *M.tuberculosis* antigens gain better access to the cytoplasm than antigens from BCG leading to more pronounced MHC class I presentation (Hess and Kaufmann, 1993). Consequently, a more effective CD8 T cell response is generated by *M.tuberculosis*. This notion was recently supported by increased MHC class I presentation of an irrelevant antigen, ovalbumin, by simultaneous *M.tuberculosis*, rather than BCG, infection of antigen presenting cells (APC) (Mazzaccaro et al., 1996).

Secreted proteins of *M.tuberculosis* comprise a valuable source of antigens for MHC class I presentation. Recently, a DNA vaccine encoding the secreted antigen Ag85A elicited MHC class I-restricted CD8 T cell responses in mice which may contribute to defence against TB (Huygen et al., 1996). In general, evidence is accumulating that immunization with secreted protein antigens of *M.tuberculosis* induce some protection against TB in guinea pigs and mice (Horwitz et al., 1995; Andersen, 1994). An important goal towards the development of improved TB vaccines based on BCG, therefore, is to augment the accessibility of secreted BCG-specific antigens to the cytoplasm of infected APC. Subsequent delivery of peptides derived from these secreted proteins into the MHC class I presentation pathway may potentiate the already existing BCG-specific immune response for preventing TB.

The phagolysosomal escape of *L.monocytogenes* represents a unique mechanism to facilitate MHC class I antigen presentation of listerial antigens (Berche et al., 1987; Portnoy et al., 1988). Listeriolysin (Hly), a pore-forming sulfhydryl-activated cytolysin, is essential for the release of *L.monocytogenes* microorganisms from phagolysosomal vacuoles into the cytosol of host cells (Gaillard et al., 1987; Portnoy et al., 1988). This escape function was recently transferred to *Bacillus subtilis* and to attenuated Salmonella ssp. strains (Bielecki et al., 1991; Gentschev et al., 1995; Hess and Kaufmann, 1997). Hly expression by an asporogenic *B.subtilis* mutant strain or in Salmonella ssp. results in bacterial escape from the phagolysosome into the cytosol of J774 macrophage-like cells (Bielecki et al., 1991; Gentschev et al., 1995; Hess and Kaufmann, 1997).

Thus, the transfer of lysosomal escape functions to heterologous microorganisms may cause an elevated toxicity of the resulting recombinant microorganisms. For this reason, the use of these lysosomal escape functions for the preparation of recombinant living vaccines has not been readily taken into consideration.

According to the present invention recombinant BCG strains secreting hemolytically active Hly were constructed which show an improved efficacy MHC class I-restricted immune response and, surprisingly, an equal or even lower cytotoxicity in comparison with the unmodified native BCG strains. Thus, these recombinant organisms are promising candidate vaccines against TB.

A first aspect of the present invention is a recombinant nucleic acid molecule encoding a fusion polypeptide comprising (a) at least one domain from a Mycobacterium polypeptide, wherein said domain is capable of eliciting an immune response in a mammal, and (b) a phagolysosomal escape domain.

A specific embodiment of this first aspect is the nucleic acid molecule in SEQ ID No.1. This nucleic acid molecule comprises a signal peptide coding sequence (nucleotide 1–120), a sequence coding for an immunogenic domain (nucleotide 121–153), a peptide linker coding sequence (nucleotide 154–210), a sequence coding for a phagolysosomal domain (nucleotide 211–1722), a further peptide linker coding sequence (nucleotide 1723–1800) and a sequence coding for a random peptide (nucleotide 1801–1870). The corresponding amino acid sequence is shown in SEQ ID No.2.

The nucleic acid of the present invention contains at least one immunogenic domain from a polypeptide derived from an organism of the genus Mycobacterium, preferably from *Mycobacterium tuberculosis* or from *Mycobacterium bovis*. This domain has a length of at least 6, preferably of at least 8 amino acids. The immunogenic domain is preferably a portion of a native Mycobacterium polypeptide. However, within the scope of the present invention is also a modified immunogenic domain, which is derived from a native immunogenic domain by substituting, deleting and/or adding one or several amino acids.

The immunogenic domain is capable of eliciting an immune response in a mammal. This immune response can be a B cell-mediated immune response. Preferably, however, the immunogenic domain is capable of eliciting a T cell-mediated immune response, more preferably a MHC class I-restricted CD8 T cell response.

The domain capable of eliciting an immune response is peferably selected from immunogenic peptides or polypeptides from *M.bovis* or *M.tuberculosis* or from immunogenic fragments thereof. Specific examples for suitable antigens are Ag85B (p30) from *M.tuberculosis* (Harth et al., 1996), Ag85B (α-antigen) from *M.bovis* BCG (Matsuo et al., 1988), Ag85A from *M.tuberculosis* (Huygen et al., 1996) and ESAT-6 from *M.tuberculosis* (Sorensen et al., 1996, Harboe et al., 1996 and Andersen et al., 1995). More preferably, the immunogenic domain is derived from the antigen Ag85B. Most preferably, the immunogenic domain comprises the sequence from aa.41 to aa.51 in SEQ ID No.2.

The recombinant nucleic acid molecule according to the present invention further comprises a phagolysosomal escape domain, i.e. a polypeptide domain which provides for an escape of the fusion polypeptide from the phagolysosome into the cytosol of mammalian cells. Preferably, the phagolysosomal escape domain is derived from an organism of the genus Listeria. More preferably, the phagolysosomal escape domain is derived from the organism *L.monocytogenes*. Most preferably, the phagolysosomal domain is encoded by a nucleic acid molecule selected from: (a) the nucleotide sequence from nucleotide 211–1722 as shown in SEQ ID No.1, (b) a nucleotide sequence which encodes for the same amino acid sequence as the sequence from (a), and (c) a nucleotide sequence hybridizing under stringent conditions with the sequence from (a) or (b).

Apart from the nucleotide sequence depicted in SEQ ID No.1 the present invention also comprises nucleic acid sequences hybridizing therewith. In the present invention the term "hybridization" is used as defined in Sambrook et al. (Molecular Cloning. A laboratory manual, Cold Spring Harbor Laboratory Press (1989), 1.101–1.104). In accordance with the present invention the term "hybridization" is used if a positive hybridization signal can still be observed after washing for one hour with 1×SSC and 0.1% SDS at 55° C., preferably at 62° C. and more preferably at 68° C., particularly for 1 hour in 0.2×SSC and 0.1% SDS at 55° C., preferably at 62° C. and more preferably at 68° C. A sequence hybridizing with a nucleotide sequence as per SEQ ID No.1 under such washing conditions is a phagolysosomal escape domain encoding nucleotide sequence preferred by the subject invention.

Preferably, the recombinant nucleic acid molecule encoding for a fusion polypeptide contains a signal peptide encoding sequence. More preferably, the signal sequence is a signal sequence active in Mycobacteria, preferably in *M.bovis*, e.g. a native *M.bovis* signal sequence. A preferred example of a suitable signal sequence is the nucleotide sequence coding for the Ag85B signal peptide which is depicted in SEQ ID No.1 from nucleotide 1 to 120.

Further, it is preferred that a peptide linker be provided between the immunogenic domain and the phagolysosomal escape domain. Preferably, said peptide linker has a length of from 5 to 50 amino acids. More preferably, a sequence encoding a linker as shown in SEQ ID No.1 from nucleotide 154 to 210 or a sequence corresponding thereto as regards the degeneration of the genetic code.

A further subject matter of the invention pertains to a recombinant vector comprising at least one copy of a nucleic acid molecule as defined above. Preferably, the recombinant vector is a prokaryotic vector, i.e. a vector containing elements for replication or/and genomic integration in prokaryotic cells. Preferably, the recombinant vector carries the nucleic acid molecule of the present invention operatively linked with an expression control sequence. The expression control sequence is preferably an expression control sequence active in Mycobacteria, particularly in *M.bovis*. The vector can be an extrachromosomal vector or a vector suitable for integration into the chromosome. Examples of such vectors are known to the man skilled in the art and, for instance, given in Sambrook et al. supra.

A still further subject matter of the invention is a cell comprising a recombinant nucleic acid molecule or a vector as defined above. Preferably, the cell is prokaryotic, particularly a Mycobacterium cell. Further, it is preferred that the cell is capable of expressing the nucleic acid molecule of the invention.

In a second aspect of the present invention a recombinant *Mycobacterium bovis* cell is provided which comprises at least one recombinant nucleic acid molecule encoding a fusion polypeptide comprising (a) at least one domain capable of eliciting an immune response in a mammal and (b) a phagolysosomal escape domain. According to this aspect, the immunogenic domain is not restricted to Mycobacterium antigens and can be selected from autoantigens, tumor antigens and pathogen antigens such as virus antigens, parasite antigens, bacterial antigens in general and immunogenic fragments thereof. Specific examples for suitable tumor antigens are human tumor antigens such as the p53 tumor suppressor gene product (Houbiers et al., 1993) and melanocyte differentiation antigens, e.g. Melan-A/ MART-1 and gp100 (van Elsas et al., 1996). Specific examples for suitable virus antigens are human tumor virus antigens such as human papilloma virus antigens, e.g. antigens E6 and E7 (Bosch et al., 1991), influenza virus antigens, e.g. influenza virus nucleoprotein (Matsui et al., 1995; Fu et al., 1997) or retroviral antigens such as HIV antigens, e.g. the HIV-1 antigens p17, p24, RT and Env (Harrer et al., 1996; Haas et al., 1996). Specific examples for suitable parasite antigens are Plasmodium antigens such as liver stage antigen (LSA-1), circumsporozoite protein (CS or allelic variants cp26 or cp29), thrombospondin related amonymous protein (TRAP), sporozoite threonine and asparagine rich protein (STARP) from *Plasmodium falciparum* (Aidoo et al., 1995) and Toxoplasma antigens such as p30 from *Toxoplasma gondii* (Khan et al., 1991; Bulow and Boothroyd, 1991). Specific examples for suitable bacterial antigens are Legionella antigens such as Major secretory protein from *Legionella pneumophila* (Blander and Horwitz, 1991).

The cell according to the invention is preferably capable of secreting the fusion polypeptide encoded by the nucleic acid molecule of the invention and of providing it in a form suitable for MHC class I-restricted antigen recognition.

In a third aspect of the present invention a recombinant *Mycobacterium bovis* cell is provided which comprises at least one nucleic acid molecule encoding a phagolysosomal escape peptide or polypeptide. Even if the phagolysosomal escape peptide or polypeptide is not fusioned with an antigen, a surprising improvement of the immunogenic properties is found.

The recombinant *Mycobacterium bovis* cell which is provided according to the present invention may contain at least one further recombinant, e.g. heterologous nucleic acid molecule encoding a peptide or polypeptide capable of eliciting an immune response in a mammal. Said further immunogenic peptide or polypeptide may be selected from Mycobacterium antigens or, in a wider sense, from autoantigens, tumor antigens, pathogen antigens and immunogenic fragments thereof. The nucleic acid molecule coding for the further peptide or polypeptide may be situated on the same vector as the fusion gene. However, it may, for example, also be situated on a different plasmid, independently of the fusion gene, or be chromosomally integrated.

Surprisingly, it was found that a Mycobacterium cell according to the present invention has an intracellular persistence in infected cells, e.g. macrophages, which is equal or less than the intracellular persistence of a corresponding native Mycobacterium cell which does not contain the recombinant nucleic acid molecule.

A still further subject matter of the present invention is a recombinant fusion polypeptide encoded by a nucleic acid molecule as defined above. The fusion polypeptide according to the invention imparts to a cell the capability of improved MHC class I-restricted antigen recognition.

The present invention also refers to a pharmaceutical composition comprising as an active agent a cell or a fusion polypeptide as defined above, optionally together with pharmaceutically acceptable diluents, carriers and adjuvants. Preferably, the composition is a living vaccine suitable for administration to a mammal, preferably a human. The actually chosen vaccination route depends on the choice of the vaccination vector. Administration may be achieved in a single dose or repeated at intervals. The appropriate dosage depends on various parameters such as the vaccinal vector itself or the route of administration. Administration to a mucosal surface (e.g. ocular, intranasal, oral, gastric, intestinal, rectal, vaginal or urinary tract) or via the parenteral route (e.g. subcutaneous, intradermal, intramuscular, intravenous or intraperitoneal) might be chosen.

Further, the present invention pertains to a method for preparing a recombinant bacterial cell as defined above. According to the first aspect, this method comprises the steps of (i) inserting a recombinant nucleic acid molecule into a bacterial cell, said nucleic acid molecule encoding a fusion polypeptide comprising (a) at least one domain from a Mycobacterium polypeptide wherein said domain is capable of eliciting an immune response in a mammal and (b) a phagolysosomal escape domain, and (ii) cultivating the cell obtained according to step (i) under suitable conditions. Preferably, a cell is obtained which is capable of expressing said nucleic acid molecule. Preferably, the cell is a *M.bovis* cell.

According to the second aspect, this method comprises the steps of (i) inserting a recombinant nucleic acid molecule into a *Mycobacterium bovis* cell, said nucleic acid molecule encoding a fusion polypeptide comprising (a) at least one domain from a polypeptide, wherein said domain is capable of eliciting an immune response in a mammal, and (b) a phagolysosomal escape domain, and (ii) cultivating the cell obtained according to (i) under suitable conditions.

According to the third aspect, this method comprises the step of (i) inserting a recombinant nucleic acid molecule into a *Mycobacterium bovis* cell, said nucleic acid molecule encoding a phagolysosomal escape peptide or polypeptide, and (ii) cultivating the cell obtained according to (i) under suitable conditions.

If desired, the method of the present invention comprises inserting at least one further recombinant nucleic acid molecule into the *Mycobacterium bovis* cell, said further recombinant nucleic acid molecule encoding a peptide or polypeptide capable of eliciting an immune response in a mammal.

Finally, the present invention relates to a method for the preparation of a living vaccine comprising formulating the recombinant cell in a pharmaceutically effective amount with pharmaceutically acceptable diluents, carriers and/or adjuvants.

The invention will be further illustrated by the following figures and sequence listings.

Figure 1B:
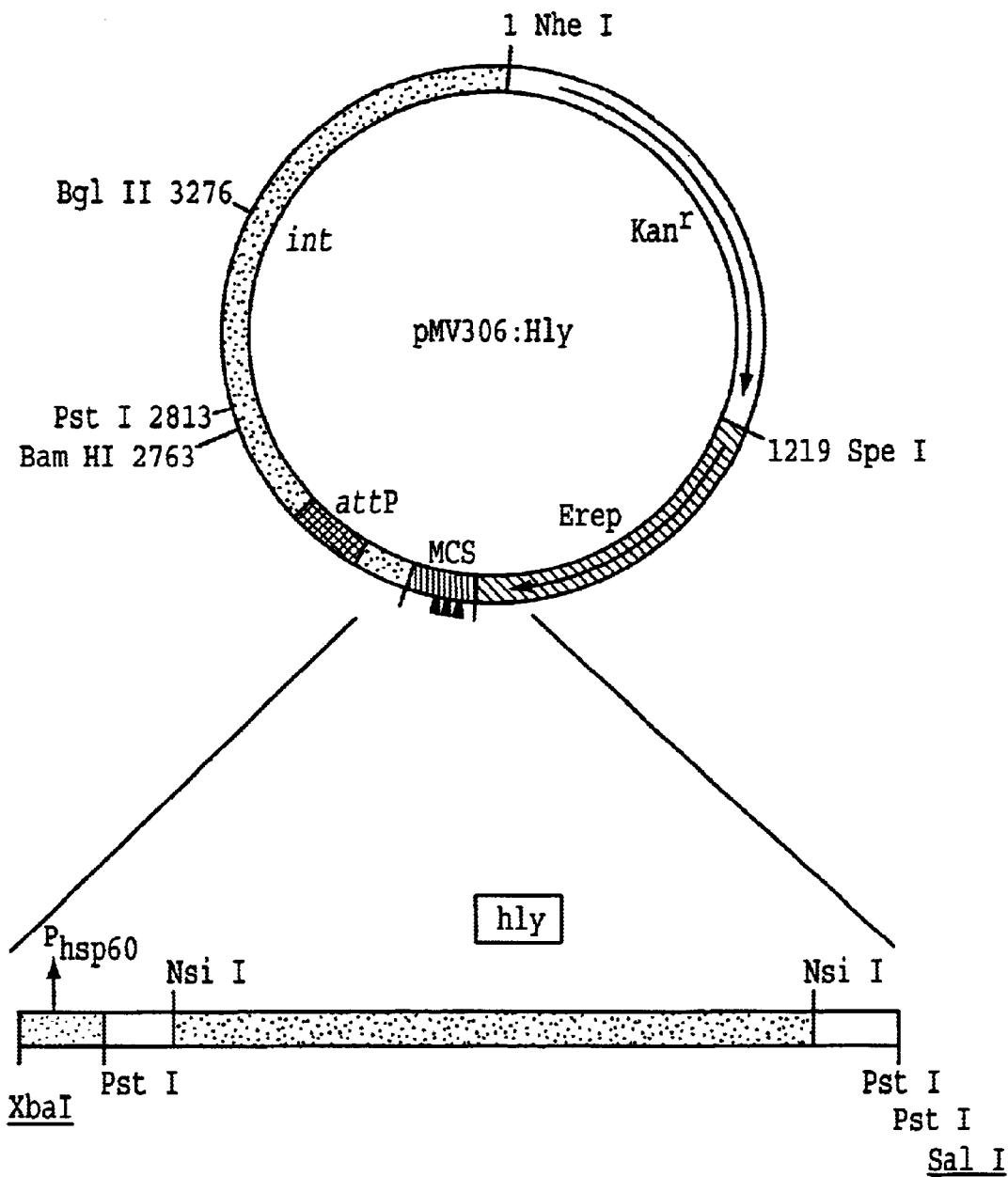

FIG. 1: shows plasmid maps for Hly secretion by recombinant BCG strains.

A. Extrachromosomal Hly expression by *Escherichia coli*—mycobacteria shuttle plasmid pAT261:Hly.

Insertion of the pILH-1—derived 1.7 kb Pst I-fragment encoding the DNA sequence of the mature Hly protein. Abbreviations: Mrep, mycobacterial replicon; Erep, *E.coli* origin of replication; kan, kanamycin-resistance gene; hsp, heat shock protein promoter.

B. Chromosomal integrative shuttle vector pMV306:Hly for Hly expression by mycobacteria. The inserted DNA-restriction fragment (Xba I-Sal I) including the hsp60 promoter is derived from plasmid pAT261:Hly. Abbreviations: attP, attachment site of mycobacteriophage L5; MCS, multiple cloning site; int, integrase of mycobacteriophage L5.

FIG. 2: shows the amino acid sequence of the Hly fusion expressed by BCG pAT261:Hly or BCG pMV306:Hly (SEQ ID NO: 2). The amino acid sequence corresponding to the hly gene-specific open reading frame is derived from the DNA sequence of the mycobacteria expression plasmids pAT261:Hly or pMV306:Hly. The Hly fusion protein consists of the following different polypeptide sequences: BCG-specific Ag85B including signal peptide, underlined amino acid sequence in single letter code, (previously termed α-antigen; Matsuo et al., 1988); *E coli* pHly 152-specific HlyA, italic letters, (Hess et al., 1986); mature Hly, bold letters, (Domann and Chakraborty, 1989); random amino acid sequence, normal letters. The restriction sites (Pst I and Nsi I) for corresponding gene fusions are presented below the amino acid sequence.

Figure 3:

FIG. 3: shows the analysis of Hly expression by recombinant BCG. Detection of Hly fusion protein in lysates (L) or supernatants (S) of BCG, BCG pAT261:Hly or BCG pMV306:Hly strains by immunostaining. Culture lysates and enriched supernatants of the different mycobacterial strains were separated on SDS/10% polyacrylamide gel and transferred to Hybond-PVDF membrane. The primary antibody used for chemiluminescent immunostaining of the 62 kDa Hly hybrid protein was anti-Hly mAb H14-3 (Nato et al, 1991).

Figure 4A:
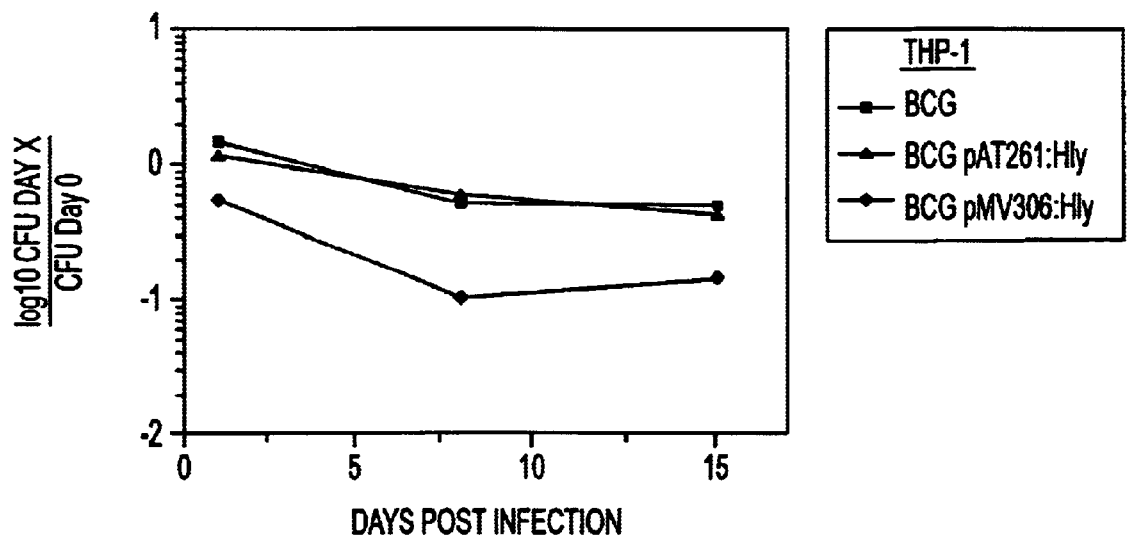
Figure 4B:
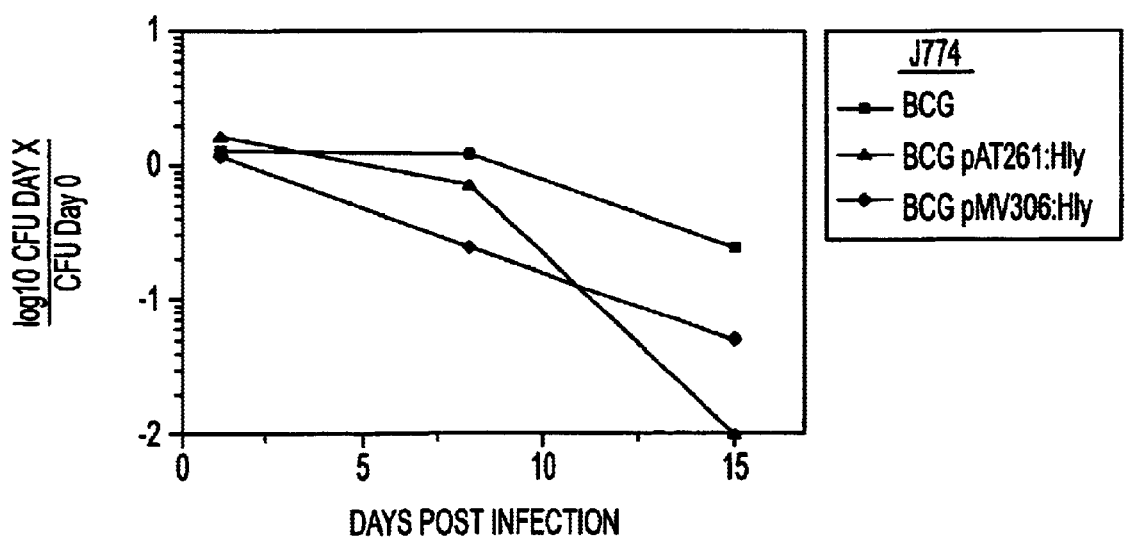
Figure 4C:
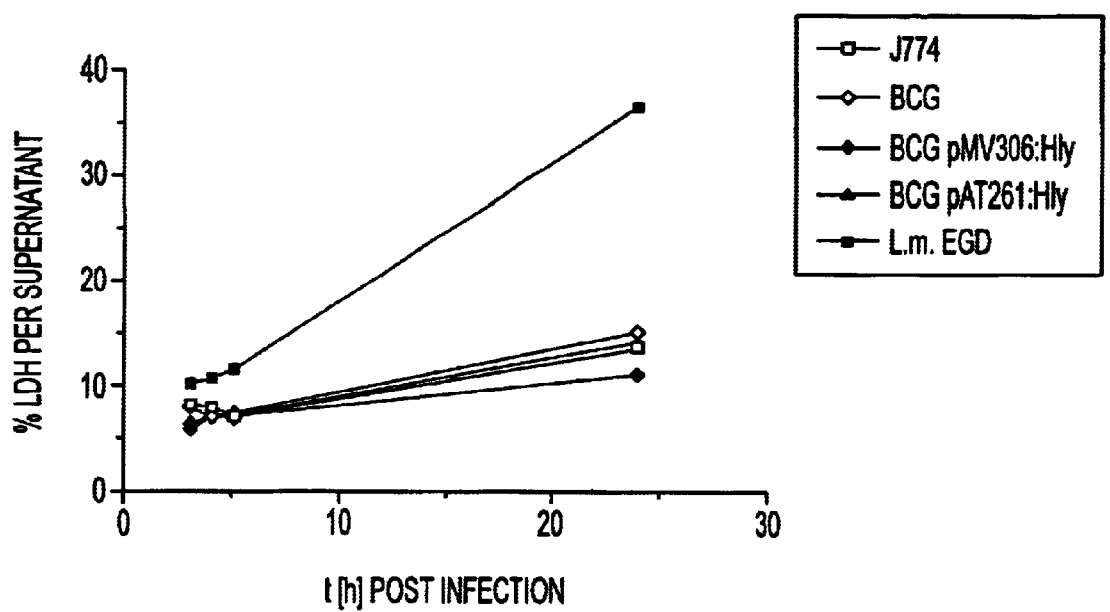

FIG. 4: shows the intracellular growth and cytotoxicity of a recombinant BCG strain.

A. Survival of wild-type BCG (■), BCG pAT261:Hly (Δ) and BCG pMV306:Hly (♦) strains in human macrophage-like cells THP-1.

B. Survival of wild-type BCG (■), BCG pAT261:Hly (Δ) and BCG pMV306:Hly (♦) strains in murine J774A.1 macrophage-like cells. At 3 h post infection, r-BCG-specific CFU were determined from infected-cell lysates and were monitored from day 0 to day 15. The data are presented as means±SD (n=3).

C. Supernatants and cell lysates of J774A.1 were assayed for LDH activity after BCG or r-BCG infection. J774A.1 (□), BCG (◇), BCG pMV306:Hly (♦), BCG pAT261:Hly (Δ) or *L.monocytogenes* EGD (■). Indicated is the cumulative percentage of total LDH activity detected in the supernatant (mean±SD). This is a representative experiment of three. The percent LDH released into the supernatant was determined as a measure of cell death.

SEQ ID No.1: shows the nucleotide sequence of a nucleic acid molecule according to the present invention.

SEQ ID No.2: shows the corresponding amino acid sequence of the nucleic acid molecule of SEQ ID No.1.

EXAMPLES

1. Experimental Procedures 1.1 Bacterial Strains and Plasmids

*M.bovis* BCG strain Chicago (ATCC 27289) was cultured in Dubos broth base (Difco) supplemented with Dubos medium albumin (Difco) at 37° C. A mid-logarithmic culture was aliquoted and stored at −70° C. until use. *L.monocytogenes* EGD Sv 1/2a (Domann and Chakraborty, 1989) originally obtained from G. B. Mackaness was grown in brain heart infusion (BHI) broth (Difco) at 37° C. with aeration. Plasmid pILH-1 was a generous gift of Drs. I. Gentschev and W. Goebel (University of Würzburg, Germany). The mycobacteria—*E.coli* shuttle vectors pAT261 and pMV306 were obtained from MedImmune (Gaithersburg, U.S.A.).

1.2 Enzymes and General Genetic Techniques

Restriction enzymes (Boehringer Mannheim) and T4 DNA ligase (Pharmacia) were used as recommended by the manufacturer. Molecular cloning and recombinant DNA techniques were performed following standard protocols (Sambrook et al., 1989).

1.3 DNA Manipulations and Sequencing

Extrachromosomal pAT261 (parental vector pAB261; Stover et al., 1993) and integrative pMV306 (parental vector pMV361; Stover et al., 1991) expression plasmids were used for Hly secretion. The plasmids pAT261 and pMV306 share common elements including an expression cassette, the Tn903-derived aph gene conferring kanamycin-resistance as a selectable marker, and an *E.coli* origin of replication derived from pUC19. They differ by the insertion of either a mycobacterial plasmid origin of replication (pAT261) or the attP and int genes of mycobacteriophage L5 (pMV306). The inserted DNA-fragment of the *M.bovis* BGC-specific Ag85B—gene in plasmid construct pAT261 is under the control of the BCG hsp60 promoter. The Pst I restriction site (position 4404, MedImmune) downstream the coding sequence for the mature Ag85B protein was used to construct Hly-derived fusions which maintain the hemolytic activity of native Hly from *L.monocytogenes* EGD and are exported by the N-terminal Ag85B-specific signal peptide. The 1.7 kb Pst I-fragment (original position 1357 and 4277; Hess et al., 1986) of the original gene fusion hly-hlyA encoded by plasmid pILH-1 (Gentschev et al., 1995; Hess et al., 1996) was used for constructing pAT261:Hly. The complete Xba I-Sal I DNA expression cassette, including hsp60 promoter, for the encoded Ag85B-Hly hybrid protein of plasmid pAT261:Hly was introduced into the plasmid pMV306. This resulting construct was termed pMV306:Hly. The correct DNA sequence of these plasmids at the sites of fragment insertion was determined using the following oligonucleotides BCG-Hly5-GCTTTGTCCTGCTG and BCG-Hly3-GGAAGTCAGGGTGA (Sequiserve, Vaterstetten, Germany). The DNA sequence analysis revealed a random insertion of a short Pst I-DNA fragment at the 3'-end of the hly-hlyA gene fusion which codes for 11 aa.

1.4 Characterization of Recombinant *M.bovis* BCG Strains

The plasmids pAT261:Hly or pMV306:Hly were introduced into *M.bovis* BCG strain Chicago by standard electroporation protocol (Langermann et al., 1994) and then recombinant colonies were selected on Middlebrook 7H10 agar supplemented with kanamycin (15 μg/ml). Kanamycin-resistant colonies were grown to mid-logarithmic phase in Dubos liquid media (Difco) containing 10% Dubos medium albumin (Difco) and 15 μg/ml kanamycin for three weeks. After washing the cells in phosphate buffered saline (PBS) plus Tween 80, the cell suspension was concentrated 20-fold in RIPA buffer (1% NP-40, 0.5% Deoxycholate, 0.1% SDS, 50 mM Tris, pH 8.0) to lyse the cells. Bacteria-free supernatant (1 ml) of these cultures were filtered through 0.2-μm membrane filters. The Hly fusion protein in the supernatant was enriched by incubation with 100 μl butyl-Sepharose (Pharmacia) for 30 min at room temperature in a rotating device (Schoel et al., 1994). After centrifugation (3000 rpm) the pellet was dissolved in Laemmli buffer (Laemmli, 1970). Subsequently proteins were separated by 10% SDS/polyacrylamide gel electrophoresis as described previously (Laemmli, 1970) and were transferred to Hybond-PVDF membranes (Amersham Life Science). Immunostainings were performed with the anti-Hly mAb H14-3 (Nato et al., 1991) and peroxidase-conjugated secondary antibodies (Boehringer Mannheim). The washing procedure and the chemiluminescent immunodetection were performed according to the manufacturer's description [BM Western Blotting Kit (Mouse/Rabbit) (Boehringer Mannheim)]. The signal development on X-ray film (Kodak, XOMAT-AR) was performed for 1 min.

The hemolytic activity of supernatants and whole-bacterial suspensions of BCG pAT261:Hly, BCG pMV306:Hly, BCG and *L.monocytogenes* were determined by serially diluting the samples in phosphate buffered saline (PBS) containing 0.1% bovine serum albumin. Diluted samples (100 μl) were subsequently activated by adding cysteine (20 mM final concentration) and were incubated at 37° C. for 45 min with 50 μl of sheep erythrocytes ($6\times10^8$ cells/ml in PBS, pH 6.0) in 96-well plates. Hemolytic activities are complete CHU, which are defined as the reciprocal value of the highest dilution at which complete hemolysis was detectable (Gentschev et al., 1995).

1.5 In vitro Analysis of Mycobacterial Growth

Human and murine macrophage-like cells THP-1 (ATCC TIB-202) and J774A.1 (ATCC TIB-67), respectively, were allowed to adhere to 24-well plates ($10^6$ per well). In case of THP-1, adherence was achieved by stimulation with 10 nM PMA (Sigma) 48 h prior to infection. Cells were infected at multiplicity of infection (moi) of 10 mycobacteria (BCG, BCG pAT261:Hly or BCG pMV306:Hly) per cell for 3 h. Immediately after infection, CFU were determined by plating serial dilutions of supernatants and cell lysates on 7H10 agar enriched with Bacto Middlebrook OADC (Difco) and appropriate 15 μg/ml kanamycin. The degree of mycobacterial uptake by macrophages were comparable. The remaining samples of infected macrophages were washed with PBS and further incubated for 14 days in the presence of 200 μg/ml gentamicin. Intracellular growth of recombinant BCG strains was determined by CFU analysis after 1, 8 or 15 days post infection (p.i.).

1.6 LDH Release

The cytotoxicity of recombinant BCG strains and of *L.monocytogenes* EGD as positive control was determined by measuring the LDH release by infected J774A.1 macrophages. The culture supernatants and cell lysates of BCG, BCG pAT261:Hly, BCG pMV306:Hly or *L.monocytogenes* EGD-infected J774A.1 macrophages were assayed for LDH activity using the quantitation kit obtained from Promega. J774A.1 cells ($10^4$ per well) were seeded into 96-well plates and infected at moi of 10. One hour after infection, gentamicin (final concentration 200 μg/ml) was added to the samples. The LDH activity was quantitatively analysed at 3, 4, 5 or 24 h p.i. according to the manufacturer's instructions. The percentage of cytotoxicity was calculated as follows: % Cytotoxicity=(J774A.1 Infected-J774A.1 Spontaneous)/(J774A.1 Maximum-J774A.1 Spontaneous×100).

2. Results 2.1 Construction of the Mycobacteria—*Escherichia coli* Shuttle Expression Vectors pAT261:Hly and pMV306:Hly In order to transfer the phagolysosomal escape function [mediated by Hly of *L.monocytogenes* EGD Sv 1/2a (Domann and Chakraborty, 1989)] to BCG Chicago two different E.coli-mycobacteria shuttle vectors pAT261 and pMV306 were used. The second-generation vector pAT261, a pMV261 derivative (Stover et al., 1991), directs extrachromosomal Hly expression with about five plasmid copies per BCG genome and the integrative plasmid pMV306, a derivation of pMV361, allows stable chromosomal expression of Hly (FIG. 1) (Stover et al., 1991).

A pILH-1-derived 1.7 kb Pst I-DNA fragment coding for an hly-hltA (E.coli pHly152-specific hemolysin A) open reading frame (ORF) was inserted into Pst I-site of plasmid pAT261 (Gentschev et al., 1995; Stover et al., 1993). This resulting gene fusion codes for the expression of secreted proteins directed to the supernatant by the BCG-specific Ag85B signal peptide (Matsuo et al., 1990). The construct was termed pAT261:Hly and its Xba I-Sal I DNA expression cassette under transcriptional control of the hsp60 mycobacterial promoter was subsequently used for insertion into the parental pMV306 vector resulting in the construct, pMV306:Hly (FIG. 1). The DNA sequence of the hly-specific insertion sites in both mycobacterial expression plamids, including the coding sequence for the BCG-specific Ag85B-signal peptide (Matsuo et al., 1990) was analysed. The derived amino acid sequence of the complete Hly fusion protein is presented in FIG. 2. The mature Hly fusion protein consists of 30 amino acids (aa) at the N-terminus and 52 aa at the C-terminal part of the fusion which originally belong to HlyA of E.coli (Gentschev et al., 1995).

Subsequently, each plasmid construct pAT261:Hly or pMV306:Hly was electroporated into BCG Chicago strain resulting in BCG pAT261:Hly or BCG pMV306:Hly with plasmid or chromosomal Hly expression, respectively.

2.2 Analysis of Hly Expression in BCG pAT261:Hly and BCG pMV306:Hly

To characterize Hly secretion by the BCG pAT261:Hly or by BCG pMV306:Hly strain appropriate supernatants and mycobacterial lysates of mid-logarithmic grown cultures were prepared according to Stover et al. (1993). The Hly fusion was enriched via hydrophobic interaction chromatography to overcome the observed cross-reactivity of anti-Hly monclonal antibodies (mAb) available for immunostaining (Schoel et al., 1994; Nato et al., 1991). The Hly fusion protein is detectable in lysates and supernatants of both mycobacterial strains, BCG pAT261:Hly and BCG pMV306:Hly (FIG. 3). The predicted size, 62 kDa, of the Hly-derived polypeptide is slightly larger than that of the original 58 kDa Hly protein of L.monocytogenes.

In order to characterize the pore-forming capacity of the Hly fusion protein secreted by BCG pAT261:Hly and BCG pMV306:Hly, the hemolytic activity of whole-bacteria suspensions and of supernatants were determined. The samples of BCG pAT261:Hly and BCG pMV306:Hly reveal hemolytic activity on sheep erythrocytes (Table 1) which formally proves successful transfer of cytolytic Hly function to mycobacterial species.

TABLE 1

Hemolytic activities of supernatant and whole-bacteria suspensions of recombinant BCG strains and L. monocytogenes EGD

| | Hemolytic activity (CHU)[a] | |
|---|---|---|
| Strain | Supernatant | Whole-bacteria suspension[b] |
| L. monocytogenes EGD | 8 | 16 |
| BCG pAT261:Hly | 2 | 4 |

TABLE 1-continued

Hemolytic activities of supernatant and whole-bacteria suspensions of recombinant BCG strains and L. monocytogenes EGD

| | Hemolytic activity (CHU)[a] | |
|---|---|---|
| Strain | Supernatant | Whole-bacteria suspension[b] |
| BCG pMV306:Hly | 2 | 4 |
| BCG | ND[c] | ND |

[a]The hemolytic activity is given in complete units (CHU), which are defined as the reciprocal of the highest dilution of complete hemolysis.
[b]Extracellular and membrane-bound hemolytic activity.
[c]ND, non-detectable.

2.3 Growth of Recombinant BCG Strains in Macrophages

Survival of BCG pAT261:Hly or BCG pMV306:Hly microorganisms in host cells was monitored by mycobacterial CFU of infected macrophages at day 1, 8 or 15 post infection (p.i.). The human monocytic cell line THP-1 (ATCC TIB-202) and the murine macrophage-like cell line J774A.1 (ATCC TIB-67) were used as mycobacterial target cells. Phorbol myristate acetate (PMA) stimulated THP-1 cells resemble native human monocyte-derived macrophages (Tsuchiya et al., 1982). Three hours after infection of THP-1 or J774A.1 cells the efficacy of mycobacterial phagocytosis was determined. Subsequent long term culture was performed in the presence of 200 µg/ml gentamicin to kill released or non-phagocytosed mycobacteria in the supernatant. As depicted in FIG. 4, each BCG strain, BCG pAT261:Hly and BCG pMV306:Hly, failed to grow in either type of host cell. Moreover, BCG pMV306:Hly bacteria showed impaired intracellular persistence in THP-1 and J774A.1 host cells as compared to the parental BCG strain. Noteworthy, the intracellular survival rate of BCG pMV306:Hly bacteria in THP-1 macrophages was already reduced at day 1 p.i. in regard to values of BCG or BCG pAT261:Hly-infected samples.

In contrast, the intracellular persistence of BCG pMV306:Hly was comparable to BCG in THP-1 (FIG. 4). Interestingly, at day 15 p.i. viable BCG pAT261:Hly bacteria were not detectable in infected J774A.1 cells suggesting complete growth inhibition of these mycobacterial constructs at least in the presence of gentamicin.

In order to gain insights into the impaired intracellular persistence of BCG pAT261:Hly and BCG pMV306:Hly strains, the cytotoxicity for J774A.1 macrophages of these recombinant BCG strains was determined in short term cultures. Cytotoxicity was analyzed by measuring lactate dehydrogenase (LDH) activity in supernatants of host cells infected with BCG; BCG pAT261:Hly; BCG pMV306:Hly; or L.monocytogenes EGD at 3, 4, 5 and 24 h p.i. At 24 h p.i. the amount of released LDH into supernatants did not significantly differ between parental BCG, BCG pAT261:Hly or BCG pMV306:Hly-infected and non-infected host cells (FIG. 4). In contrast, the fast-growing and hemolytic L.monocytogenes EGD strain caused profound LDH release into the supernatant within 24 h p.i. These data suggest that secretion of hemolytic Hly by recombinant BCG strains did not alter the cytotoxicity of the parental BCG strain. Rather, both BCG pAT261:Hly and BCG pMV306:Hly strains showed impaired persistence in murine macrophages as compared to the non-recombinant BCG carrier.

REFERENCES

Aidoo, M., Lalvani, A., Allsopp, C. E. M. et al. (1995), Identification of conserved antigenic components for a cytotoxic T lymphocyte-inducing vaccine against malaria, The Lancet 345: 1003.

Andersen, P. (1994), Effective vaccination of mice against *Mycobacterium tuberculosis* infection with a soluble mixture of secreted mycobacterial protein, Infect. Immun. 62: 2536–2544.

Andersen, P., Andersen, A. B., Sorensen, A. L. and Nagai, S. (1995), Recall of long-lived immunity to *Mycobacterium tuberculosis* infection in mice, J. Immunol. 154: 3359.

Berche, P., Gaillard, J. L., and Sansonetti, P. J. (1987), Intracellular growth of *L.monocytogenes* as a prerequisite for in vivo induction of T cell-mediated immunity, J. Immunol. 138: 2266–2276.

Bielecki, J., Youngman, P., Connelly, P., and Portnoy, D. A. (1990), *Bacillus subtilus* expressing a hemolysin gene from *Listeria monocytogenes* can grow in mammalian cells, Nature 354: 175–176.

Blander, S. J. and Horwitz, M. A. (1991), Vaccination with a major secretory protein of Legionelia induces humoral and cell-mediated immune responses and protective immunity across different serogroups of *Legionella pneumophila* and different species of Legionella, J. Immunol. 147: 285.

Bosch, F. X., Durst, M., Schwarz, E., Boukamp, P., Fusenig, N. E. and zur Hausen, H. (1991), The early genes E6 and E7 of cancer associated human papilloma viruses as targets of tumor suppression?, Behring Inst. Mitt. 108.

Bulow, R. and Boothroyd, J. C. (1991), Protection of mice from fatal *Toxoplasma gondii* infection by immunization with p30 antigen in liposomes, J. Immunol. 147: 3496.

Clemens, D. L., and Horwitz, M. A. (1996), The *Mycobacterium tuberculosis* phagosome interacts with early endosomes and is accessible to exogenously administered transferrin, J. Exp. Med. 184: 1349–1355.

Darji, A., Chakraborty, T., Wehland, J., and Weiss, S. (1996), Listeriolysin generates a route for the presentation of exogenous antigens by major histocompatibility complex class I, Eur. J. Immunol. 25: 2967–2971.

Domann, E., and Chakraborty, T. (1989), Nucleotide sequence of the listeriolysin gene from a *Listeria monocytogenes* serotype 1/2a strain, Nucleic Acids Res. 17: 6406.

Flesch, I., Hess, J. H., Oswald, I. P., and Kaufmann, S. H. E. (1994), Growth inhibition of *Mycobacterium bovis* by IFN-γ stimulated macrophages: regulation by endogenous tumor necrosis factor-α and by IL-10, Int. Immunol. 6: 693–700.

Flynn, J. L., Goldstein, M. M., Triebold, K. J., Keller, B., and Bloom, B. R. (1992), Major histocompatibility complex class I-restricted T cells are required for resistance to *Mycobacterium tuberculosis* infection, Proc. Natl. Acad. Sci. USA 89: 12013–12017.

Fu, T. M., Friedman, A., Ulmer, J. B., Liu, M. A. and Donnelly, J. J. (1997), Protective cellular immunity: cytotoxic T-lymphocyte responses against dominant and recessive epitopes of influenza virus nucleoprotein induced DNA immunization, J. Virol. 71: 2715.

Gaillard, J. L., Berche, P., Mounier, J., Richard, S., and Sansonetti, P. J. (1987), In vitro model of penetration and intracellular growth of *Listeria monocytogenes* in the human enterocyte-like cell line Caco-2, Infect. Immun. 55: 2822–2829.

Gentschev, I., Sokolovic, Z., Mollenkopf, H.-J., Hess, J., Kaufmann, S. H. E., Kuhn, M., Krohne, G. F., and Goebel, W. (1995), Salmonella secreting active listeriolysin changes its intracellular localization, Infect. Immun. 63: 4202–4205.

Grange, J. M. (1996), Epidemiological aspects of drug resistance, in Mycobacteria and human disease, Arnold, London, pp. 124–125.

Haas, G., Plikat, U., Debre, P., Lucchiari, M., Katlama, C., Dudoit, Y., Bonduelle, O., Bauer, M., Ihlenfeldt, H. G., Jung, G., Maier, B., Meyerhans, A. and Autran, B. (1996), Dynamics of viral variants in HIV-1 Nef and specific cytotoxic T lymphocytes in vivo, J. Immunol. 157: 4212.

Harboe, M., Oettinger, T., Wiker, H. G. et al. (1996), Evidence for occurrence of the ESAT-6 protein in *Mycobacterium tuberculosis* and virulent *Mycobacterium bovis* and for its absence in *Mycobacterium bovis* BCG, Infect. Immun. 64: 16.

Harrer, T., Harrer, E., Kalams, S. A., Barbosa, P., Trocha, A., Johnson, R. P., Elbeik, T., Feinberg, M. B., Buchbinder, S. P. and Walker, B. D. (1996), Cytotoxic T lymphocytes in asymptomatic long-term nonprogressing HIV-1 infection. Breadth and specificity of the response and relation to in vivo viral quasispecies in a person with prolonged infection and low viral load, J. Immunol. 156: 2616.

Harth, G., Lee, B.-Y., Wang. J., Clemens, D. L., and Horwitz, M. A. (1996), Novel insights into the genetics, biochemistry, and immunocytochemistry of the 30-kilodalton major extracellular protein of *Mycobacterium tuberculosis*, Infect. Immun. 64: 3038–3047.

Hess, J., Wels, W., Vogel, M., and Goebel, W. (1986), Nucleotide sequence of plasmid-encoded hemolysin determinant and its comparison with a corresponding chromosomal hemolysin sequence, FEMS Lett. 34: 1–11.

Hess, J., and Kaufmann, S. H. E. (1993), Vaccination strategies against intracellular microbes, FEMS Microbiol. Immunol. 7: 95–103.

Hess, J., Gentschev, I., Miko, D., Welzel, M., Ladel, C., Goebel, W., and Kaufmann, S. H. E. (1996), Superior efficacy of secreted over somatic p60 or listeriolysin antigen display in recombinant Salmonella vaccine induced protection against listeriosis, Proc. Natl. Acad. Sci. USA 93: 1458–1463.

Hess, J, and Kaufmann, S. H. E. (1997), Principles of cell-mediated immunity underlying vaccination strategies against intracellular pathogens, in Host Response to Intracellular Pathogens, S. H. E. Kaufmann (ed), R. G. Landes Co., Austin, pp. 75–90.

Horwitz, M. A., Lee, B.-W. E., Dillon, B. J., and Harth, G. (1995), Protective immunity against tuberculosis induced by vaccination with major extracellular proteins of *Mycobacterium tuberculosis*, Proc. Natl. Acad. Sci. USA 92: 1530–1534.

Houbiers, J. G. A., Nijman, H. W., van der Burg, S. H., Drijfhout, J. W., Kenemans, P., van de Velde, C. J. H., Brand, A., Momburg, F., Kast, W. M. and Melief, C. J. M. (1993), In vitro induction of human cytotoxic T lymphocyte responses against peptides of mutant and wild-type p53, Eur. J. Immunol. 23: 2072.

Huygen, K., Content, J., Denis, O., Montgomery, D. L., Yawman, A. M., Deck, R. R., DeWitt, C. M., Orme, I. M., Baldwin, S., D'Souza, C., Drowart, A., Lozes, E., Vandenbussche, P., Van Vooren, J.-P., Liu, M. A., and Ulmer, J. B. (1996), Immunogenicity and protective efficacy of a tuberculosis DNA vaccine, Nat. Med. 2: 893–898.

Kaufmann, S. H. E. (1993), Immunity to intracellular bacteria, Annu. Rev. Immunol. 11: 129–163.

Khan, I. A., Ely,. K. H. and Kasper, L. H. (1991), A purified parasite antigen (p30) mediates CD8 T cell immunity against fatal *Toxoplasma gondii* infection in mice, J. Immunol. 147: 3501.

King, C. H., Mundayoor, S., Crawford, J. T. and Shinnik, T. M. (1993), Expression of contact-dependent cytolytic activity by *Mycobacterium tuberculosis* and isolation of the genomic locus that encodes the activity, Infect. Immun. 61: 2708–2712.

Kochi, A. (1991), The global tuberculosis situation and the new control strategy of the World Health Organization, Tubercle 72: 1–6.

Ladel, C. H., Daugelat, S., and Kaufmann, S. H. E. (1995), Immune response to *Mycobacterium bovis* bacille Calmette Guérin infection in major histocompatibility complex class I- and II-deficient knock-out mice: contribution of CD4 and CD8 T cells to acquired resistance, Eur. J. Immunol. 25: 377–384.

Laemmli, U. K. (1970), Cleavage of structural proteins during the assembly of the head of bacteriophage T4, Nature 227: 680–685.

Langermann, S., Palaszynski, S. R., Buriein, J. E., Koenig, S., Hanson, M. S., Briles, D. E., and Stover, C. K. (1994), Protective humoral response against pneumococcal infection in mice elicited by recombinant Bacille Calmette-Guérin vaccines expressing pneumococcal surface protein A., J. Exp. Med. 180: 2277–2286.

Matsui, M., Moots, R. J., Warburton, R. J., Peace-Brewer, A., Tussey, L. G., Quinn, D. G., McMichael, A. J. and J. A. Frelinger (1995), Genetic evidence for differences between intracellular peptides of influenza A matrix peptide-specific CTL recognition, J. Immunol. 154: 1088.

Matsuo, K., Yamaguchi, R., Yamazaki, A., Tasaka, H., Terasaka, K., and Yamada, T. (1990), Cloning and expression of the *Mycobacterium bovis* BCG gene for extracellular alpha antigen, J. Bacteriol. 170: 3847–3854.

Mazzaccaro, R. Z., Gedde, M., Jensen, E. R., Van Santen, H. M., Ploegh H. L., Rock, K. L., and Bloom, B. R. (1996), Major histocompatibility class I presentation of soluble antigen facilitated by *Mycobacterium tuberculosis* infection, Proc. Natl. Acad. Sci. USA 93: 11786–11791.

McDonough, K. A., Kress, Y., and Bloom, B. R. (1993), Pathogenesis of tuberculosis: Interaction of *Mycobacterium tuberculosis* with macrophages, Infect. Immun. 61: 2763–2773.

Murray, P. J., Aldovini, A., and Young, R. A. (1996), Manipulation and potentiation of anti-mycobacterial immunity using recombinant bacille Calmette-Guérin strains that secrete cytokines, Proc. Natl. Acad. Sci. USA 93: 934–939.

Nato, F., Reich, K., Lhopital, S., Rouye, S., Geoffroy, C., Mazie, J. C., and Cossart, P. (1991), Production and characterization of neutralizing and non-neutralizing monoclonal antibodies against listeriolysin O., Infect. Immun. 59: 4641–4646.

Portnoy, D. A., Jacks, P. S., and Hinrichs, D. J. (1988), Role of hemolysin for the intracellular growth of *Listeria monocytogenes*, J. Exp. Med. 167: 1459–1471.

Roche, P. W., Triccas, J. A., and Winter, N. (1995), BCG vaccination against tuberculosis: past disappointments and future hopes, Trends Microbiol. 3: 397–401.

Russell, D. G. (1995), Mycobacterium and Leishmania: stowaways in the endosomal network. Trends in Cell Biology 5: 125–128.

Sambrook, J., Fritsch, E. F., and Maniatis, T. (1989), Molecular cloning: a laboratory manual, 2nd edition, Cold Spring Harbor Laboratory Press, New York.

Schoel, B., Welzel, M., and Kaufmann, S. H. E. (1994), Hydrophobic interaction chromatography for the purification of cytolytic bacterial toxins, J. Chromatography A 667: 131–139.

Sorensen, A. L., Nagai, S., Houen, G., Andersen, P. and Andersen, A. B. (1995), Purification and characterization of a low-molecular-mass-T-cell antigen secreted by *Mycobacterium tuberculosis*, Infect. Immun. 63: 1710.

Stover, C. K., Bansal, G. P., Hanson, M. S. Burlein, J. E., Palaszynski, S. R., Young, J. F., Koenig, S., Young, D. B., Sadziene, A., Barbour, A. G. (1993), Protective immunity elicited by recombinant Bacille Calmette Guérin (BCG) expressing outer surface protein A (OspA) lipoprotein: A candidate lyme disease vaccine, J. Exp. Med. 178: 197–209.

Stover, C. K., de la Cruz, V. F., Fuerst, T. R., Burlein, J. E., Benson, L. A., Bennett, L. T., Bansal, G. P., Young, J. F., Lee, M. H., Hatfull, G. F., Snapper, S. B., Barletta, R. G., Jacobs, W. R., Jr., and Bloom, B. R. (1991), New use of BCG for recombinant vaccines, Nature 351: 456–460.

Sturgill-Koszycki, S., Schlesinger, P. H., Chakraborty, P., Haddix, P. L., Collins, H. L., Fok, A. K., Allen, R. D., Gluck, S. L., Heuser, J. and Russell, D. G. (1994), Lack of acidification in Mycobacterium phagosomes produced by exclusion of the vesicular proton-ATPase, Science 263: 678–681.

Towbin, H., Staehelin, T., and Gordon, J. (1979), Electrophoretic transfer of proteins from polyacrylamide gels to nitrocellulose sheets: procedure and some applications, Proc. Natl. Acad. Sci. USA 76: 4350–4354.

Tsuchiya, S., Kobayashi, Y., Goto, Y., Okumura, H., Nakae, S., Konno, T., and Tada, K. (1982), Induction of maturation in cultured human monocytic leukemia cells by a phorbol diester, Cancer Res. 42: 1530–1536.

Tweten, R. K. (1995), Pore-forming toxins of gram-positive bacteria, in Virulence Mechanisms of Bacterial Pathogens, J. A. Roth et al. (ed), American Society for Microbiology, Washington, D.C., pp. 207–228.

van Elsas, A., van der Burg, S. H., van der Minne, C. E., Borghi, M., Mourer, J. S., Melief, C. J. M. and Schrier, P. I. (1996), Peptide-pulsed dendritic cells induce tumoricidal cytotoxic T lymphocytes from healthy donors against stably HLA-A⁻0201-binding peptides from Melan-A/MART-1 self antigen, Eur. J. immunol. 26: 1683.

What is claimed is:

1. A recombinant nucleic acid molecule encoding a fusion polypeptide, said fusion polypeptide comprising
   (a) at least one domain from a Mycobacterium polypeptide, wherein said domain is for eliciting an immune response in a mammal, and
   (b) a Listeria phagolysosomal escape domain.

2. The nucleic acid molecule according to claim 1, wherein said Listeria phagolysosomal escape domain is encoded by a nucleic acid molecule selected from the group consisting of:
   (a) the nucleotide sequence from nucleotide 211–1722 as shown in SEQ ID NO: 1,
   (b) a degenerate nucleotide sequence encoding an amino acid sequence corresponding to the nucleotide sequence of (a), and
   (c) a nucleotide sequence hybridizing under stringent conditions with the nucleotide sequence of (a) or (b).

3. The nucleic acid molecule according to claim 1, wherein the domain for eliciting an immune response is a peptide or polypeptide for eliciting MHC class I-restricted CD8 T cell responses.

4. The nucleic acid molecule according to claim 1, wherein the domain for eliciting an immune response is selected from the group consisting of Mycobacterium antigens Ag85B (*M. tuberculosis*), Ag85B (*M. bovis*), Ag85A (*M. tuberculosis*) and ESAT-6 (*M. tuberculosis*), or an immunogenic fragment thereof.

5. The nucleic acid molecule according to claim 4, wherein the domain for eliciting an immune response is the antigen Ag85B or an immunogenic fragment thereof.

6. The nucleic acid molecule according to claim 1, wherein the fusion polypeptide is preceded by a signal peptide sequence.

7. The nucleic acid molecule according to claim 1, wherein a peptide linker is located between the domain for eliciting an immune response and the phagolysosomal domain.

8. A recombinant vector comprising at least one copy of a nucleic acid molecule according to claim 1.

9. The vector according to claim 8, wherein said nucleic acid molecule is operatively linked with an expression control sequence.

10. The vector according to claim 9, wherein said expression control sequence is active in Mycobacteria.

11. The vector according to claim 8, which is an extrachromosomal vector.

12. The vector according to claim 8, which is a chromosomal vector.

13. A cell which comprises a recombinant nucleic acid molecule according to claim 1.

14. A cell which comprises a vector according to claim 8.

15. An *M. bovis* cell comprising a recombinant nucleic acid molecule according to claim 1.

16. A recombinant *Mycobacterium bovis* cell, comprising at least one recombinant nucleic acid molecule encoding a fusion polypeptide, said fusion polypeptide comprising
   (a) at least one domain from a Mycobacterium polypeptide and for eliciting an immune response in a mammal and
   (b) a Listeria phagolysosomal escape domain.

17. The cell according to claim 16, wherein the domain for eliciting an immune response is selected from the group consisting of autoantigens, tumor antigens, virus antigens, parasite antigens and bacterial antigens, or immunogenic fragments thereof.

18. The cell according to claim 16, wherein said cell expresses said at least one recombinant nucleic acid molecule.

19. The cell according to claim 16, wherein said cell secretes a polypeptide encoded by said at least one nucleic acid molecule.

20. The cell according to claim 16, having an intracellular persistence in infected macrophages which is equal or less than the intracellular persistence of a native Mycobacterium cell.

21. A method for preparing a recombinant bacterial cell according to claim 15 comprising the steps:
   (i) inserting a recombinant nucleic acid molecule into a bacterial cell, said nucleic acid molecule encoding a fusion polypeptide comprising
      (a) at least one domain from a Mycobacterium polypeptide, wherein said domain is for eliciting an immune response in a mammal, and
      (b) a phagolysosomal escape domain, and
   (ii) cultivating the cell obtained from step (i) under suitable conditions.

22. A method for preparing a recombinant bacterial cell according to claim 16 comprising the steps:
   (i) inserting a recombinant nucleic acid molecule into a *Mycobacterium bovis* cell, said nucleic acid molecule encoding a fusion polypeptide comprising (a) at least one domain from a polypeptide, wherein said domain is capable of eliciting an immune response in a mammal, and (b) a phagolysosomal escape domain, and
   (ii) cultivating the cell obtained according to (i) under suitable conditions.

23. A composition comprising a cell according to claim 16 and a pharmaceutically acceptable adjuvant.

24. A recombinant *Mycobacterium bovis* cell comprising at least one recombinant nucleic acid molecule encoding a Listeria phagolysosomal escape peptide or polypeptide.

25. The cell according to claim 24, further comprising at least one recombinant nucleic acid molecule encoding a peptide or polypeptide for eliciting an immune response in a mammal.

26. A method for preparing a recombinant bacterial cell according to claim 25 comprising the steps:
   (i) inserting a recombinant nucleic acid molecule into a *Mycobacterium bovis* cell, said nucleic acid molecule encoding a phagolysosomal escape peptide or polypeptide and
   (ii) cultivating the cell obtained from step (i) under suitable conditions.

27. The method of claim 26, comprising inserting at least one other recombinant nucleic acid molecule into the *Mycobacterium bovis* cell, said recombinant nucleic acid molecule encoding a peptide or polypeptide for eliciting an immune response in a mammal.

28. The method of claim 27, wherein said peptide or polypeptide for eliciting an immune response is selected from the group consisting of autoantigens, tumor antigens, virus antigens, parasite antigens and bacterial antigens, or immunogenic fragments thereof.

29. An immunogenic polypeptide comprising (a) at least one domain from a Mycobacterium polypeptide, wherein said domain elicits an immune response in a mammal, and (b) a Listeria phagolysosomal escape domain.

30. A composition comprising a polypeptide according to claim 29, and a pharmaceutically acceptable adjuvant.

31. A recombinant nucleic acid molecule encoding a fusion polypeptide, said fusion polypeptide comprising
   (a) at least one domain from a Mycobacterium polypeptide, wherein said domain is for eliciting an immune response in a mammal, and
   (b) a Listeria phagolysosomal escape domain encoded by a nucleic acid molecule selected from the group consisting of:
      (i) the nucleotide sequence from nucleotide 211–1722 as shown in SEQ ID NO: 1,
      (ii) a degenerate nucleotide sequence encoding an amino acid sequence corresponding to the nucleotide sequence of (a), and
      (iii) a nucleotide sequence hybridizing under stringent conditions with the nucleotide sequence of (a) or (b).

32. A recombinant nucleic acid molecule encoding a fusion polypeptide, said fusion polypeptide comprising
   (a) at least one domain from a Mycobacterium polypeptide, wherein said domain is for eliciting an immune response in a mammal, and
   (b) a phagolysosomal escape domain encoded by a nucleic acid molecule selected from the group consisting of:
      (i) the nucleotide sequence from nucleotide 211–1722 as shown in SEQ ID NO: 1.

33. A recombinant nucleic acid molecule encoding a fusion polypeptide, said fusion polypeptide comprising
   (a) at least one domain from a Mycobacterium polypeptide, wherein said domain is for eliciting an immune response in a mammal and said domain is selected from the group consisting of Mycobacterium antigens Ag85B (*M. tuberoulosis*), Ag85B (*M. bovis*), Ag85A (*M.tuberculosis*) and ESAT-6 (*M. tuberculosis*), or an immunogenic fragment thereof, and
   (b) a Listeria phagolysosomal escape domain.

* * * * *

SEQUENCE LISTING

<160> NUMBER OF SEQ ID NOS: 2

<210> SEQ ID NO 1
<211> LENGTH: 1881
<212> TYPE: DNA
<213> ORGANISM: Artificial Sequence
<220> FEATURE:

<223> OTHER INFORMATION: Description of Artificial Sequence: recombinant
      nucleic acid molecule comprising a domain of
      Mycobacterium and a phagolysomal escape domain
<221> NAME/KEY: CDS
<222> LOCATION: (1)..(1878)

<400> SEQUENCE: 1

```
atg aca gac gtg agc cga aag att cga gct tgg gga cgc cga ttg atg        48
Met Thr Asp Val Ser Arg Lys Ile Arg Ala Trp Gly Arg Arg Leu Met
 1               5                  10                  15 atc ggc acg gca gcg gct gta gtc ctt ccg ggc ctg gtg ggg ctt gcc        96
Ile Gly Thr Ala Ala Ala Val Val Leu Pro Gly Leu Val Gly Leu Ala
            20                  25                  30 ggc gga gcg gca acc gcg ggc gcg ttc tcc cgg ccg ggg ctg ccg gtc       144
Gly Gly Ala Ala Thr Ala Gly Ala Phe Ser Arg Pro Gly Leu Pro Val
        35                  40                  45 gag tac ctg cag tct gca aag caa tcc gct gca aat aaa ttg cac tca       192
Glu Tyr Leu Gln Ser Ala Lys Gln Ser Ala Ala Asn Lys Leu His Ser
    50                  55                  60 gca gga caa agc acg aaa gat gca tct gca ttc aat aaa gaa aat tca       240
Ala Gly Gln Ser Thr Lys Asp Ala Ser Ala Phe Asn Lys Glu Asn Ser
65                  70                  75                  80 att tca tcc atg gca cca cca gca tct ccg cct gca agt cct aag acg       288
Ile Ser Ser Met Ala Pro Pro Ala Ser Pro Pro Ala Ser Pro Lys Thr
                85                  90                  95 cca atc gaa aag aaa cac gcg gat gaa atc gat aag tat ata caa gga       336
Pro Ile Glu Lys Lys His Ala Asp Glu Ile Asp Lys Tyr Ile Gln Gly
            100                 105                 110 ttg gat tac aat aaa aac aat gta tta gta tac cac gga gat gca gtg       384
Leu Asp Tyr Asn Lys Asn Asn Val Leu Val Tyr His Gly Asp Ala Val
        115                 120                 125 aca aat gtg ccg cca aga aaa ggt tac aaa gat gga aat gaa tat att       432
Thr Asn Val Pro Pro Arg Lys Gly Tyr Lys Asp Gly Asn Glu Tyr Ile
    130                 135                 140 gtt gtg gag aaa aag aag aaa tcc atc aat caa aat aat gca gac att       480
Val Val Glu Lys Lys Lys Lys Ser Ile Asn Gln Asn Asn Ala Asp Ile
145                 150                 155                 160 caa gtt gtg aat gca att tcg agc cta acc tat cca ggt gct ctc gta       528
Gln Val Val Asn Ala Ile Ser Ser Leu Thr Tyr Pro Gly Ala Leu Val
                165                 170                 175 aaa gcg aat tcg gaa tta gta gaa aat caa cca gat gtt ctc cct gta       576
Lys Ala Asn Ser Glu Leu Val Glu Asn Gln Pro Asp Val Leu Pro Val
            180                 185                 190 aaa cgt gat tca tta aca ctc agc att gat ttg cca ggt atg act aat       624
Lys Arg Asp Ser Leu Thr Leu Ser Ile Asp Leu Pro Gly Met Thr Asn
        195                 200                 205 caa gac aat aaa atc gtt gta aaa aat gcc act aaa tca aac gtt aac       672
Gln Asp Asn Lys Ile Val Val Lys Asn Ala Thr Lys Ser Asn Val Asn
    210                 215                 220 aac gca gta aat aca tta gtg gaa aga tgg aat gaa aaa tat gct caa       720
Asn Ala Val Asn Thr Leu Val Glu Arg Trp Asn Glu Lys Tyr Ala Gln
225                 230                 235                 240 gct tat cca aat gta agt gca aaa att gat tat gat gac gaa atg gct       768
Ala Tyr Pro Asn Val Ser Ala Lys Ile Asp Tyr Asp Asp Glu Met Ala
                245                 250                 255 tac agt gaa tca caa tta att gcg aaa ttt ggt aca gca ttt aaa gct       816
Tyr Ser Glu Ser Gln Leu Ile Ala Lys Phe Gly Thr Ala Phe Lys Ala
            260                 265                 270 gta aat aat agc ttg aat gta aac ttc ggc gca atc agt gaa ggg aaa       864
Val Asn Asn Ser Leu Asn Val Asn Phe Gly Ala Ile Ser Glu Gly Lys
        275                 280                 285
```

```
atg caa gaa gaa gtc att agt ttt aaa caa att tac tat aac gtg aat     912
Met Gln Glu Glu Val Ile Ser Phe Lys Gln Ile Tyr Tyr Asn Val Asn
290                 295                 300 gtt aat gaa cct aca aga cct tcc aga ttt ttc ggc aaa gct gtt act     960
Val Asn Glu Pro Thr Arg Pro Ser Arg Phe Phe Gly Lys Ala Val Thr
305                 310                 315                 320 aaa gag cag ttg caa gcg ctt gga gtg aat gca gaa aat cct cct gca    1008
Lys Glu Gln Leu Gln Ala Leu Gly Val Asn Ala Glu Asn Pro Pro Ala
                325                 330                 335 tat atc tca agt gtg gcg tat ggc cgt caa gtt tat ttg aaa tta tca    1056
Tyr Ile Ser Ser Val Ala Tyr Gly Arg Gln Val Tyr Leu Lys Leu Ser
                340                 345                 350 act aat tcc cat agt act aaa gta aaa gct gct ttt gat gct gcc gta    1104
Thr Asn Ser His Ser Thr Lys Val Lys Ala Ala Phe Asp Ala Ala Val
                355                 360                 365 agc gga aaa tct gtc tca ggt gat gta gaa cta aca aat atc atc aaa    1152
Ser Gly Lys Ser Val Ser Gly Asp Val Glu Leu Thr Asn Ile Ile Lys
370                 375                 380 aat tct tcc ttc aaa gcc gta att tac gga ggt tcc gca aaa gat gaa    1200
Asn Ser Ser Phe Lys Ala Val Ile Tyr Gly Gly Ser Ala Lys Asp Glu
385                 390                 395                 400 gtt caa atc atc gac ggc aac ctc gga gac tta cgc gat att ttg aaa    1248
Val Gln Ile Ile Asp Gly Asn Leu Gly Asp Leu Arg Asp Ile Leu Lys
                405                 410                 415 aaa ggc gct act ttt aat cga gaa aca cca gga gtt ccc att gct tat    1296
Lys Gly Ala Thr Phe Asn Arg Glu Thr Pro Gly Val Pro Ile Ala Tyr
                420                 425                 430 aca aca aac ttc cta aaa gac aat gaa tta gct gtt att aaa aac aac    1344
Thr Thr Asn Phe Leu Lys Asp Asn Glu Leu Ala Val Ile Lys Asn Asn
                435                 440                 445 tca gaa tat att gaa aca act tca aaa gct tat aca gat gga aaa att    1392
Ser Glu Tyr Ile Glu Thr Thr Ser Lys Ala Tyr Thr Asp Gly Lys Ile
450                 455                 460 aac atc gat cac tct gga gga tac gtt gct caa ttc aac att tct tgg    1440
Asn Ile Asp His Ser Gly Gly Tyr Val Ala Gln Phe Asn Ile Ser Trp
465                 470                 475                 480 gat gaa gta aat tat gat cct gaa ggt aac gaa att gtt caa cat aaa    1488
Asp Glu Val Asn Tyr Asp Pro Glu Gly Asn Glu Ile Val Gln His Lys
                485                 490                 495 aac tgg agc gaa aac aat aaa agc aag cta gct cat ttc aca tcg tcc    1536
Asn Trp Ser Glu Asn Asn Lys Ser Lys Leu Ala His Phe Thr Ser Ser
                500                 505                 510 atc tat ttg cca ggt aac gcg aga aat att aat gtt tac gct aaa gaa    1584
Ile Tyr Leu Pro Gly Asn Ala Arg Asn Ile Asn Val Tyr Ala Lys Glu
                515                 520                 525 tgc act ggt tta gct tgg gaa tgg tgg aga acg gta att gat gac cgg    1632
Cys Thr Gly Leu Ala Trp Glu Trp Trp Arg Thr Val Ile Asp Asp Arg
530                 535                 540 aac tta cca ctt gtg aaa aat aga aat atc tcc atc tgg ggc acc acg    1680
Asn Leu Pro Leu Val Lys Asn Arg Asn Ile Ser Ile Trp Gly Thr Thr
545                 550                 555                 560 ctt tat ccg aaa tat agt aat aaa gta gat aat cca atc gaa tat gca    1728
Leu Tyr Pro Lys Tyr Ser Asn Lys Val Asp Asn Pro Ile Glu Tyr Ala
                565                 570                 575 tta gcc tat gga agt cag ggt gat ctt aat cca tta att aat gaa atc    1776
Leu Ala Tyr Gly Ser Gln Gly Asp Leu Asn Pro Leu Ile Asn Glu Ile
                580                 585                 590 agc aaa atc att tca gct gca gtt ctt tcc tct tta aca tcg aag cta    1824
Ser Lys Ile Ile Ser Ala Ala Val Leu Ser Ser Leu Thr Ser Lys Leu
                595                 600                 605
```

```
cct gca gag ttc gtt agg cgc gga tcc gga att cga agc tta tcg atg    1872
Pro Ala Glu Phe Val Arg Arg Gly Ser Gly Ile Arg Ser Leu Ser Met
    610                 615                 620 tcg acg tag                                                         1881
Ser Thr
625

<210> SEQ ID NO 2
<211> LENGTH: 626
<212> TYPE: PRT
<213> ORGANISM: Artificial Sequence
<220> FEATURE:
<223> OTHER INFORMATION: Description of Artificial Sequence: recombinant

<400> SEQUENCE: 2

Met Thr Asp Val Ser Arg Lys Ile Arg Ala Trp Gly Arg Arg Leu Met
 1               5                  10                  15

Ile Gly Thr Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Ser Ala Lys Gln Ser Ala Ala Asn Lys Leu His Ser
    50                  55                  60

Ala Gly Gln Ser Thr Lys Asp Ala Ser Ala Phe Asn Lys Glu Asn Ser
65                  70                  75                  80

Ile Ser Ser Met Ala Pro Pro Ala Ser Pro Ala Ser Pro Lys Thr
                85                  90                  95

Pro Ile Glu Lys Lys His Ala Asp Glu Ile Asp Lys Tyr Ile Gln Gly
            100                 105                 110

Leu Asp Tyr Asn Lys Asn Asn Val Leu Val Tyr His Gly Asp Ala Val
        115                 120                 125

Thr Asn Val Pro Pro Arg Lys Gly Tyr Lys Asp Gly Asn Glu Tyr Ile
    130                 135                 140

Val Val Glu Lys Lys Lys Lys Ser Ile Asn Gln Asn Asn Ala Asp Ile
145                 150                 155                 160

Gln Val Val Asn Ala Ile Ser Ser Leu Thr Tyr Pro Gly Ala Leu Val
                165                 170                 175

Lys Ala Asn Ser Glu Leu Val Glu Asn Gln Pro Asp Val Leu Pro Val
            180                 185                 190

Lys Arg Asp Ser Leu Thr Leu Ser Ile Asp Leu Pro Gly Met Thr Asn
        195                 200                 205

Gln Asp Asn Lys Ile Val Val Lys Asn Ala Thr Lys Ser Asn Val Asn
    210                 215                 220

Asn Ala Val Asn Thr Leu Val Glu Arg Trp Asn Glu Lys Tyr Ala Gln
225                 230                 235                 240

Ala Tyr Pro Asn Val Ser Ala Lys Ile Asp Tyr Asp Asp Glu Met Ala
                245                 250                 255

Tyr Ser Glu Ser Gln Leu Ile Ala Lys Phe Gly Thr Ala Phe Lys Ala
            260                 265                 270

Val Asn Asn Ser Leu Asn Val Asn Phe Gly Ala Ile Ser Glu Gly Lys
        275                 280                 285

Met Gln Glu Glu Val Ile Ser Phe Lys Gln Ile Tyr Tyr Asn Val Asn
    290                 295                 300

Val Asn Glu Pro Thr Arg Pro Ser Arg Phe Phe Gly Lys Ala Val Thr
305                 310                 315                 320
```

-continued

```
Lys Glu Gln Leu Gln Ala Leu Gly Val Asn Ala Glu Asn Pro Pro Ala
            325                 330                 335

Tyr Ile Ser Ser Val Ala Tyr Gly Arg Gln Val Tyr Leu Lys Leu Ser
            340                 345                 350

Thr Asn Ser His Ser Thr Lys Val Lys Ala Ala Phe Asp Ala Ala Val
            355                 360                 365

Ser Gly Lys Ser Val Ser Gly Asp Val Glu Leu Thr Asn Ile Ile Lys
    370                 375                 380

Asn Ser Ser Phe Lys Ala Val Ile Tyr Gly Gly Ser Ala Lys Asp Glu
385                 390                 395                 400

Val Gln Ile Ile Asp Gly Asn Leu Gly Asp Leu Arg Asp Ile Leu Lys
                405                 410                 415

Lys Gly Ala Thr Phe Asn Arg Glu Thr Pro Gly Val Pro Ile Ala Tyr
            420                 425                 430

Thr Thr Asn Phe Leu Lys Asp Asn Glu Leu Ala Val Ile Lys Asn Asn
            435                 440                 445

Ser Glu Tyr Ile Glu Thr Thr Ser Lys Ala Tyr Thr Asp Gly Lys Ile
    450                 455                 460

Asn Ile Asp His Ser Gly Gly Tyr Val Ala Gln Phe Asn Ile Ser Trp
465                 470                 475                 480

Asp Glu Val Asn Tyr Asp Pro Glu Gly Asn Glu Ile Val Gln His Lys
                485                 490                 495

Asn Trp Ser Glu Asn Asn Lys Ser Lys Leu Ala His Phe Thr Ser Ser
            500                 505                 510

Ile Tyr Leu Pro Gly Asn Ala Arg Asn Ile Asn Val Tyr Ala Lys Glu
    515                 520                 525

Cys Thr Gly Leu Ala Trp Glu Trp Trp Arg Thr Val Ile Asp Asp Arg
    530                 535                 540

Asn Leu Pro Leu Val Lys Asn Arg Asn Ile Ser Ile Trp Gly Thr Thr
545                 550                 555                 560

Leu Tyr Pro Lys Tyr Ser Asn Lys Val Asp Asn Pro Ile Glu Tyr Ala
            565                 570                 575

Leu Ala Tyr Gly Ser Gln Gly Asp Leu Asn Pro Leu Ile Asn Glu Ile
            580                 585                 590

Ser Lys Ile Ile Ser Ala Ala Val Leu Ser Ser Leu Thr Ser Lys Leu
    595                 600                 605

Pro Ala Glu Phe Val Arg Arg Gly Ser Gly Ile Arg Ser Leu Ser Met
    610                 615                 620

Ser Thr
625
```